United States Patent [19]

Nelkin

[11] 4,416,272
[45] Nov. 22, 1983

[54] COMBINATION UNDERPANT AND HERNIAL TRUSS

[75] Inventor: Nedwyn R. Nelkin, Overland Park, Kans.

[73] Assignee: H. G. Enterprises, Kansas City, Mo.

[21] Appl. No.: 257,236

[22] Filed: Apr. 24, 1981

[51] Int. Cl.³ .............................................. A61F 5/24
[52] U.S. Cl. ...................................... 128/96; 128/99; 128/100
[58] Field of Search ................... 128/96, 95, 99, 100, 128/101, 98; 2/400, 401, DIG. 7

[56] References Cited

U.S. PATENT DOCUMENTS

| | | | |
|---|---|---|---|
| 1,612,121 | 12/1926 | Hittenberger | 128/96 |
| 2,022,751 | 12/1935 | Waksmundzka | 2/41 |
| 2,605,762 | 8/1952 | Balistrieri | 128/96 |
| 3,021,838 | 2/1962 | Fine | 128/96 |
| 3,308,813 | 3/1967 | Loeffel | 128/96 |
| 3,454,003 | 7/1969 | Kleber-Sailhen | 128/96 |
| 3,486,501 | 12/1969 | Erickson et al. | 128/96 |
| 3,524,449 | 8/1970 | Peters | 128/524 |
| 3,577,986 | 5/1971 | Regent | 128/96 |
| 4,059,103 | 11/1977 | Glaser | 128/96 |

*Primary Examiner*—C. Fred Rosenbaum
*Assistant Examiner*—C. W. Shedd
*Attorney, Agent, or Firm*—Litman, Day & McMahon

[57] ABSTRACT

A combination underpant and hernial truss comprises a brief having front, rear and crotch portions with spaced leg holes. A truss pad is attached to the front portion and protrudes inwardly of the brief to engage and support a herniated abdominal area. An adjustable length belt encircles the brief and is connected to the front portion adjacent the pad for directing hernia retaining force thereon. The belt is free from securement to the rear portions of the brief for selective movement upwardly and downwardly to adjust to the wearer's comfort.

7 Claims, 4 Drawing Figures

COMBINATION UNDERPANT AND HERNIAL TRUSS

This invention relates to hernial trusses, and in particular, to a combination underpant and hernial truss which provides both support and comfort to a wearer.

BACKGROUND OF THE INVENTION

Many devices have been employed and proposed in the nature of trusses for the wearer's relief and comfort from reduceable inguinal hernias, however, most such devices have been cumbersome, unsightly, uncomfortable strap truss arrangements which hernia sufferers are often reluctant to don. Moreover, the proper balance of support and comfort is lacking in many previous truss arrangements wherein, if the truss is easy to don and comfortable to wear, the hernial area is not held sufficiently secure. Conversely, if the hernial area was held securely, the truss was not easy to put on or comfortable to wear. Additionally, previous truss arrangements generally required usage of a conventional undergarment for sanitary purposes and, in many cases, the wearing of the truss made donning conventional undergarments difficult. Previous truss arrangements generally left unsightly bulges and lines from a multitude of straps to show through outer garments.

OBJECTS OF THE INVENTION

The principle objects of the present invention are: to provide a combination underpant and hernial truss; to provide such a combination underpant and truss wherein the underpant is in the form of a brief of elastic material providing support for the hernial area; to provide such a combination underpant and truss having hernia retaining pads built into the underpant; to provide such a combination underpant and truss having an adjustable belt encircling same for control of inward pressure to be applied upon the herniated areas; to provide such a combination underpant and truss in which the belt is attached only at a front portion of the brief and is free at a rear portion of the brief for selective movement upwardly and downwardly to adjust to the wearer's comfort; to provide such an underpant and truss in which the encircling belt is attached only to the front portion at certain areas of the hernia pads to apply even pressure across the area of the pads and press same inwardly toward the hernial areas for secure retention; and to provide such a combination underpant and truss which is relatively inexpensive, light weight, cool, washable, comfortable and relatively well adapted for the intended purpose.

Other objects and advantages of this invention will become apparent from the following description taken in connection with the accompanying drawings wherein are set forth, by way of illustration and example, certain embodiments of this invention.

DESCRIPTION OF THE PREFERRED EMBODIMENT

Figure 1:
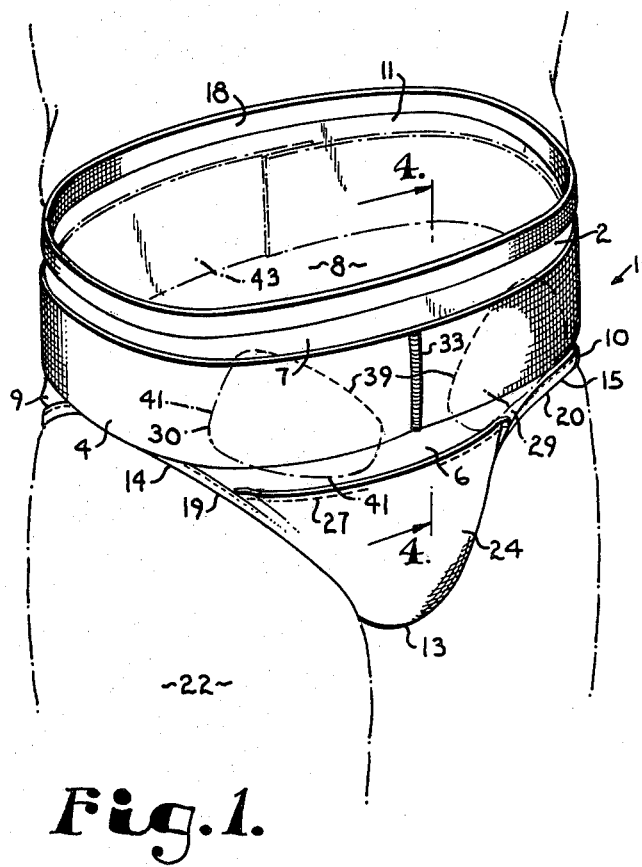
FIG. 1 is a front perspective view of the combination underpant and hernial truss embodying the present invention and shown on the body of a wearer.

As required, a detailed embodiment of the present invention is disclosed herein, however, it is to be understood that the disclosed embodiment is merely exemplary of the invention which may be embodied in various forms, therefore, specific structural and functional details disclosed herein are not to be interpreted as limiting, but merely as a basis for the claims and as a representative basis for teaching one skilled in the art to variously employ the present invention in virtually any appropriately detailed structure.

Figure 4:
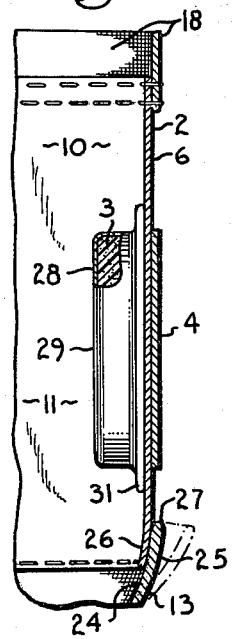
FIG. 4 is sectional view taken along lines 4—4, FIG. 1.

Referring to the drawings in more detail:

The reference numeral 1 generally indicates a combination underpant and hernial truss embodying the present invention. The combination underpant and truss 1 generally includes an underpant in the form of a brief 2 with hernial area support pads 3 emplaced therein, FIG. 4, and pulled into the hernial area by the combined action of the brief 2 and a waist encircling belt 4. The belt 4 is generally attached to the brief only at the brief front portion and is free to move upwardly and downwardly at the rear portion of the brief to adjust to the wearer's comfort.

In the illustrated example, the underpant brief 2 is preferably of a supportive, elastic material such as manufactured under the registered trademark Spandex and provides a comfortable, lightweight, cool, washable material with elasticity to provide inward pressure and support for the wearer's body. The brief has fabric panels defining an open top and including a front portion 6 with a central area 7, a rear portion 8 and opposite side portions 9 and 10 joining the front and rear portions 6 and 8. The brief has inner and outer surfaces 11 and 12 with the inner surface 11 contacting the body of the wearer. A crotch portion 13 also connects the front and rear portions 6 and 8 and, in combination with the respective side portions 9 and 10, defines spaced leg holes 14 and 15.

The brief 2 has a waist encircling top band 18 and respective leg hole encircling bands 19 and 20 attached to the fabric of the brief 2 as by sewing. Preferably, the bands 18, 19 and 20 are of elastic material for snug fitting of the brief with the body of the wearer 22.

The brief 2 may be adapted for use by either males or females, and in the illustrated example, the crotch portion 13 of the brief is particularly adapted for male use and has an open mesh fabric genital pocket 24 sewn therein with an upper margin 25 overlying a downward flap 26 of the brief front portion 6. The pocket upper margin 25 and flap 26 are generally secured together, as by sewing, and in the illustrated example, the sewing 27, FIG. 1, only extends partially inwardly from the leg holes 14 and 15, thereby retaining an unsewn or open portion 27 substantially centrally located which may be opened for communication of the brief interior with the exterior for male urination.

The hernia pads 3 are attached to the brief 2 and, in the illustrated example, spaced pads are provided for support and protection of right, left, or double hernia simply by the provision of a pad either on the left side or right side of the brief front or on both sides. The pad or pads 3 are each substantially oblong and somewhat triangular in shape, and are oriented on the front portion 6 of the brief whereby the pad longitudinal axis slants downwardly and the pad apex is located toward the brief crotch portion 13 for effective coverage of the abdominal hernial area or areas. Each pad 3 is preferably of a resilient material such as foam rubber and has opposite, substantially flat surfaces 28 for comfort.

In the illustrated example, the brief 2 has two pads 3 therein, as for reduction of double hernia. The front portion 6 has fabric envelopes or pockets 29 and 30 protruding inwardly from the inner surface 11 of the brief 2 with each pocket having a surrounding flange portion 31 attached to the inner surface as by sewing. The pads 3 are encapsulated or received within each of the pockets 29 and 30 and positioned in the appropriate area for hernial engagement when the brief is donned.

Figure 3:
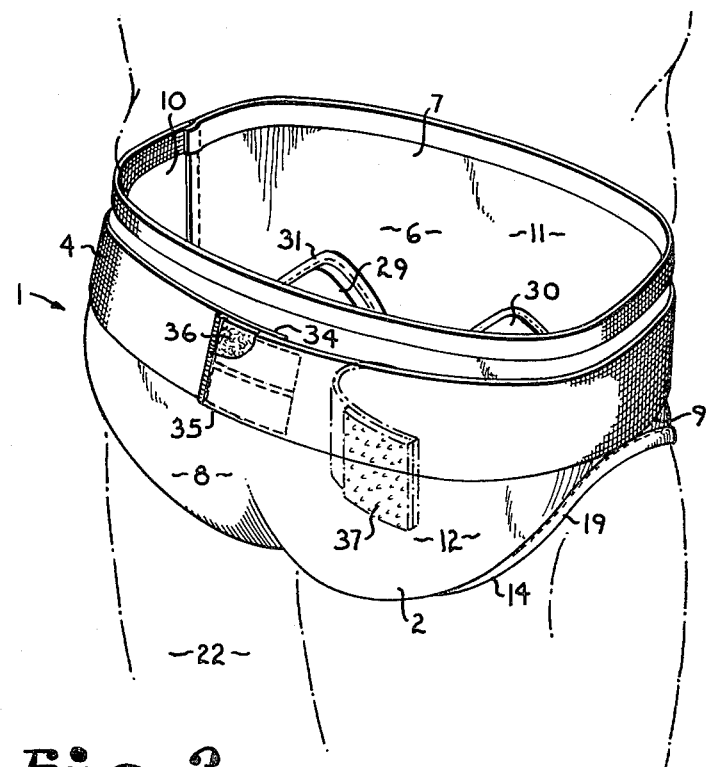
FIG. 3 is a rear perspective view of the combination underpant and truss.

The belt 4 encircles the brief 2 outwardly of the front and rear portions 6 and 7 and in the illustrated example, is relatively wide and of a longitudinally elastic material. The belt 4 may be either of one or multiple-piece construction as required for material availability and ease of manufacture and, in the illustrated example, is of two-piece construction joined at a sewn center section 33. Separable end portions 34 and 35, FIG. 3, are positioned at the backside of the wearer and located generally at the brief rear portion 8. A closure means is provided for adjusting the length of the belt 4, such as hook and loop pile fabric fastening patches 36 and 37 which coordinate to detachably connect and are available, for example, under the registered trademark Velcro of the American Velcro Company. The belt 4 is secured to the brief 2 only at the front portion 6 whereby the portion of the belt at the back side of the wearer 22 can be moved up and down relative to the brief rear portion 8 to adjust to the wearer's comfort. In the illustrated example, the belt 4 is secured to the front portion 6 adjacent each of the pad pockets 29 and 30 as by sewing thereto, and particularly secured to respective edge portions 39 of the pockets 29 and 30 adjacent the central area 7 of the front portion 6. Bottom edge portions 40 and side edge portions 41 of each of the pad pockets 29 and 30 are not secured to the belt 4 whereby the belt upon tensioning tends to pull from the edge portions 39 smoothly across the pad pockets 29 and 30 and evenly press the respective pads into secure engagement with the abdominal hernia areas in proper anatomical curvature for effective support and comfort. Upon tensioning, the belt 4 does not tend to pucker over the pads 3 and cause the pads to move from a flat position and dig a corner or edge into the hernial area which would impart discomfort and soreness to an already tender area.

Figure 2:
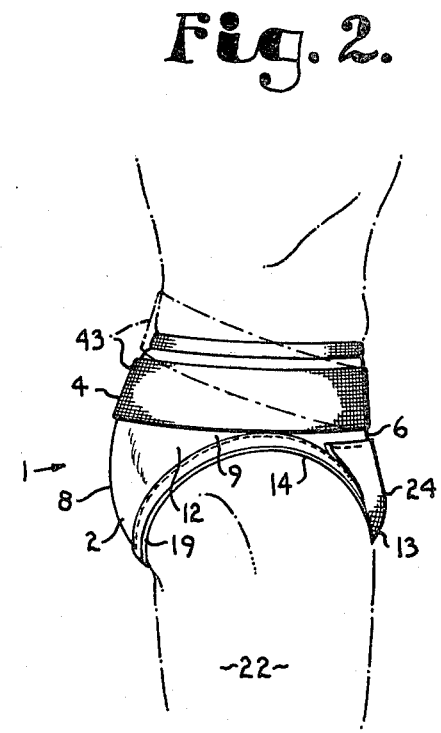
FIG. 2 is a side elevational view of the combination underpant and truss on a body of a wearer.

As the belt 4 at a back portion 43 is not attached to the brief 2, the wearer can easily pull the belt back portion 43 upwardly or downwardly to adjust to particular body configurations and positions, such as reclining, sitting or standing. Further, a wearer of relatively slim build such as shown in FIG. 2, may desire to position the belt back portion 43 fairly low upon the hips or just above the hip line as indicated by the phantom lines. Conversely, the wearer of heavy or obese build may desire to position the back portion 43 at a substantially upward angle to exert an upward pull upon the pad or pads 3 and conform the engagement of the pad and hernial area to a sagging or inclined abdominal surface.

In the use of the combination underpant and hernial truss 1, the herniated person manually reduces the rupture area by pushing protruding organs inwardly through the ruptured abdominal wall. Next, the person steps into the brief 2 and pulls the same up into the proper fitting position as he or she would any conventional brief. The person centers the pads 3 on the ruptured openings and then, standing straight upwardly, takes one of the belt end portions 34 or 35 in each hand and pulls same out and around to his or her backside to attach the closure means. The belt is adjusted in length until it fits comfortably snug and the pads fit securely over the point of rupture. Further, adjustment of the belt back 43 is made upwardly or downwardly and the belt length is further adjusted as necessary to adjust to the comfort of the wearer.

It is to be understood that while one form of this invention has been illustrated and described, it is not to be limited to the specific form or arrangement of parts herein described and shown, except insofar as such limitations are included in the following claims.

What is claimed and desired to secure by Letters Patent is:

1. A combination underpant and hernial truss comprising:
   (a) an underpant brief having front, rear and crotch portions and spaced legholes separated by said crotch portion;
   (b) said front portion having a truss pad connected thereto and protruding inwardly of said brief to engage and support an abdominal hernial area of the body of a wearer;
   (c) a belt and a means for adjusting the tension of said belt, said belt encircling said brief and being secured to said front portion near a lateral center thereof and substantially adjacent said pad for directing hernia retaining force thereon; said belt being free from securement to said rear portion so as to allow selective movement upwardly and downwardly relative to said rear portion to adjust to the wearer's comfort.

2. The combination underpant and truss set forth in claim 1 wherein:
   (a) said brief is constructed of supportive elastic material tending to pull said pad inwardly toward said hernial area;
   (b) said belt is constructed of longitudinally elastic material further tending to pull said pad inwardly toward said hernial area.

3. The combination underpant and truss set forth in claim 1 wherein:
   (a) said brief has a waist encircling top band and respective leghole encircling bands, all of elastic material; and
   (b) said belt is elastic and sufficiently wide to cover substantially all of said truss pad.

4. The combination underpant and truss set forth in claim 1 wherein:
   (a) said belt has separable end portions located adjacent said brief rear portion; and
   (b) means for adjusting the tension of said belt include hook and loop faric fastening patches on respective said end portions.

5. A combination underpant and hernial truss comprising:
   (a) an underpant brief of supportive, elastic material having front, rear and crotch portions which space legholes;
   (b) said brief having a waist encircling top band and respective leghole encircling bands, all of elastic material;
   (c) said brief front portion having spaced truss pads connected thereto and protruding inwardly of said brief to engage abdominal hernial areas of the body of a wearer with the elastic material of said brief having a memory tending to pull said pads inwardly toward said hernial areas; and
(d) a relatively wide belt of longitudinally elastic material encircling said brief outwardly of said front and rear portions; said belt being attached to said brief only at said front portion adjacent the brief midline between said pads so as to direct an inwardly pulling force particularly to said pads; said belt having separably connectible end portions located adjacent said brief rear portion and respectively having hook and loop fabric fastening patches attached thereto for adjustably tensioning said belt; said belt being selectively movable upwardly and downwardly relative to said brief rear portion to adjust the hernial truss to the wearer's comfort.

6. The combination underpant and truss set forth in claim 5 wherein:
(a) said brief has inner and outer surfaces and opposite side portions at the respective junctures of said front and rear portions with said front portion having a center area;
(b) said brief front portion has spaced oblong pockets connected to the inner surface of said front portion and protruding inwardly thereof with respective sides of said pockets adjacent said center area, said pads are oblong and respectively emplaced in said pockets with the respective longitudinal axes thereof slanted toward said crotch portion;
(c) said belt is sewn to said front portion only at said center area adjacent the respective sides of said pockets, such that said belt tends to pull smoothly across said pads upon tensioning of said belt and to apply even pressure to press said pads inward toward the wearer's hernial areas.

7. A combination underpant and hernial truss comprising:
(a) an underpant brief having front, rear and crotch portions and spaced legholes separated by said crotch portion;
(b) said brief having inner and outer surfaces and opposite side portions at the respective junctures of said front and rear portions with said front portion having a center area;
(c) a trust pad attached to the inner surface of said front portion and protruding inwardly thereof to engage and support a hernial area of the body of a wearer, said pad having a side adjacent said center area;
(d) a belt of longitudinally elastic material encircling said brief outwardly of said front and rear portions and attached to said brief only within said center area, said belt being free from securement to said brief rear portion and flexible so as to allow selective movement upward and downward whereat said belt overlies said brief rear portion to allow the user to adjust the belt to be comfortable, said belt substantially overlying said pad and thereby tending to pull smoothly across said pad and apply even pressure to move said pad inward toward the wearer's hernial area.

* * * * *